United States Patent [19]

Kobayashi et al.

[11] Patent Number: 4,503,232

[45] Date of Patent: Mar. 5, 1985

[54] METHOD FOR THE PREPARATION OF α-KETOAMIDE IMINES

[75] Inventors: Toshiaki Kobayashi; Masato Tanaka, both of Yatabe, Japan

[73] Assignee: Agency of Industrial Science & Technology, Tokyo, Japan

[21] Appl. No.: 423,182

[22] Filed: Sep. 24, 1982

[30] Foreign Application Priority Data

Apr. 24, 1982 [JP] Japan .................................. 57-69175

[51] Int. Cl.³ .......................................... C07D 213/36
[52] U.S. Cl. .................................... 546/336; 546/337; 548/561; 548/495; 548/341; 548/342; 549/76; 549/496; 564/164; 564/191; 560/35
[58] Field of Search .................. 560/35; 564/163, 164, 564/191; 542/417, 418; 548/341, 342, 495, 561, 568; 549/496; 546/336, 337

[56] References Cited

U.S. PATENT DOCUMENTS 4,152,352  5/1979  Perron ............................ 260/465 D
4,203,896  5/1980  Koppel et al. ...................... 548/188
4,338,467  7/1982  Takano et al. ...................... 568/428

OTHER PUBLICATIONS

Harada et al., "Bulletin of the Chemical Society of Japan", vol. 44, No. 4, pp. 1068-1071 (1971).
Harada et al., "Bulletin of the Chemical Society of Japan", vol. 32, pp. 1794-1800 (1967).
Valentine, Jr. et al., "Asymmetric Synthesis", pp. 329-342 (1978), Synthesis.

Primary Examiner—Jane T. Fan
Attorney, Agent, or Firm—Birch, Stewart, Kolasch & Birch

[57] ABSTRACT

The invention provides a novel method for the preparation of an α-ketoamide imine having a characteristic structure expressed by the formula

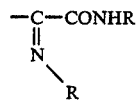

in which R is a group such as an alkyl, aryl or the like group, in a one-step reaction in which a halogen-containing organic compound reacts with a primary amine and carbon monoxide in the presence of a carbonylation catalyst. The product compound is useful as an intermediate for the synthesis of various kinds of organic compounds including medicines and agricultural chemicals.

14 Claims, No Drawings

METHOD FOR THE PREPARATION OF α-KETOAMIDE IMINES

BACKGROUND OF THE INVENTION

The present invention relates to a method for the preparation of an α-ketoamide imine by the reaction of a halogen-containing organic compound, a primary amine and carbon monoxide in the presence of a carbonylation catalyst.

α-ketoamide imines include a class of compounds useful as intermediates for the synthesis of various medicines and agricultural chemicals or, in particular, industrially important compounds in the synthetic preparation of amino acids. The starting compounds for the synthetic preparation of the compounds of this class are, in the prior art, usually an α-keto-acid and a primary amine but this process has not yet been applied to the industrial preparation of amino acids due to the expensiveness of the α-keto-acids. On the other hand, amino acids are usually prepared either by fermentation or by chemical synthesis. In the latter method of chemical synthesis, one of the most important problems to be solved is in the synthetic route to form the portion

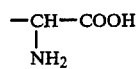

in an amino acid

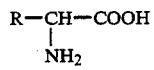

in order to establish a generally applicable method for the preparation of amino acids. No generally applicable and economically advantageous method, however, has yet been established for the synthetic preparation of amino acids starting from a halogen-containing organic compound which is usually inexpensive and available in large quantities.

In view of the above mentioned problems in the synthetic preparation of amino acids, the inventors have conducted extensive research and, as a result thereof, have arrived at the discovery of a novel and very interesting reaction, in which one mole of a halogen-containing organic compound reacts in one step with two moles of carbon monoxide in the presence of a primary amine to form an α-ketoamide imine having a structure expressed by the formula

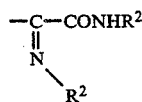

as a precursory structure for the formation of the structure of the formula

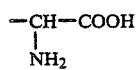

in the amino acid. The inventors concentrated on this novel reaction which resulted in the completion of the present invention.

SUMMARY OF THE INVENTION

The present invention provides a novel and efficient method for the preparation of an α-ketoamide imine comprising a reaction in which a halogen-containing organic compound, which is inexpensive and available in large industrial quantities, reacts with a primary amine and carbon monoxide.

Accordingly, an object of the present invention is to provide a method for the preparation of an α-ketoamide imine from inexpensive starting materials which are available in large industrial quantities.

Another object of the present invention is to provide a method in which a wide variety of α-ketoamide imines can be produced readily in a one-step reaction.

A further object of the present invention is to provide a method for the preparation of an α-ketoamide imine in a reaction which can be performed readily and without the necessity of undertaking a troublesome reaction procedure or using starting materials having too high reactivity.

Other and further objects, features and advantages of the invention will appear more fully from the following description.

DETAILED DESCRIPTION OF THE PREFERRED EMBODIMENTS

More particularly, the present invention relates to a method for the preparation of an α-ketoamide imine represented by the general formula

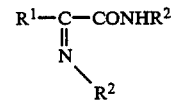

in which $R^1$ is a monovalent hydrocarbon group selected from the class consisting of alkyl, aryl, aralkyl, cycloalkyl and alkenyl groups or a heterocyclic group and $R^2$ is a monovalent hydrocarbon group selected from the group consisting of alkyl, aryl, aralkyl and cycloalkyl groups or a heterocyclic group, which comprises reacting a halogen-containing organic compound represented by the general formula $R^1X$, in which $R^1$ has the same meaning as defined above and X is a halogen atom, a primary amine represented by the general formula $R^2NH_2$, in which $R^2$ has the same meaning as defined above, and carbon monoxide in the presence of a carbonylation catalyst.

The above mentioned reaction for the synthetic preparation of an α-ketoamido imine according to the inventive method is expressed by the following reaction equation:

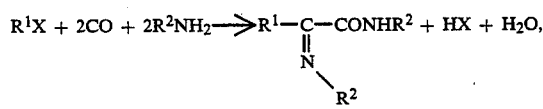

in which the symbols $R^1$, $R^2$ and X each have the same meaning as defined above.

The group denoted by $R^1$ in the halogen-containing organic compound used in the inventive method is a monovalent hydrocarbon group selected from the group consisting of alkyl, cycloalkyl, aryl, aralkyl and alkenyl groups or a heterocyclic group and these organic groups may be substituted with one or more of various kinds of functional groups or atoms excepting hydroxy, carboxyl, amino and monoalkylamino groups. Suitable substituent groups or atoms include, for example, dialkylamino groups, carbamoyl group, acyl groups, alkoxy groups, alkoxycarbonyl groups, halogen atoms, sulfonyl group, thioalkoxy groups, sulfinyl group, sulfenyl group, cyano group, acyloxy groups, disilyl groups, nitro group, epoxy group, formyl group and the like. The halogen atom X in the halogen-containing organic compound $R^1X$ is preferably a chlorine, bromine or iodine atom.

Particular halogen-containing organic compounds suitable in the above mentioned reaction according to the invention are exemplified by halobenzene derivatives such as bromobenzene, iodobenzene, bromonaphthalene, 4-iodoanisole, 4-acetylbromobenzene and the like, halogenated derivatives of ethylene such as 62 bromostyrene, ethyl β-bromoacrylate, 2-bromo-2- butene, 2-methyl-1-bromo-1-propene, 2-bromopropene, 2-methylthio-1-bromoethylene and the like, halomethane derivatives such as benzyl chloride, ethyl chloroacetate, chloromethylimidazole, chloroacetamide, 3-chloromethylindole and the like and halogen-containing heterocyclic compounds derived from furan, thiophene, pyrrole, pyridine and the like as well as various kinds of substituted compounds derived from the above named halogen-containing organic compounds.

Any kind of primary amines represented by the formula $R^2NH_2$ can be used in the reaction of the inventive method without particular limitations and the primary amine can be selected freely according to the objective α-ketoamide imine. The organic group denoted by $R^2$ is exemplified by alkyl groups such as methyl, ethyl, propyl, butyl and the like groups, cyclohexyl group, benzyl group and aryl groups such as phenyl 4-tolyl and the like groups.

In the reaction according to the present invention, the formation of the α-ketoamide imine is accompanied by a hydrogen halide produced as a by-product, which is captured by the amine as the reactant. In this case, however, it is also an advantageous embodiment of the inventive method that a tertiary amine is added to the reaction mixture conjunctively with the primary amine as the reactant so that the hydrogen halide may be captured by this tertiary amine. Triethyl amine, tributyl amine and the like are named as the examples of such a tertiary amine although there is no particular limitations on the kind or structure of the tertiary amine provided that the tertiary amine has a stronger basicity than the primary amine used as the reactant.

The catalyst used in the present invention per se is a conventionally known carbonylation catalyst widely used in various kinds of carbonylation reactions such as the oxo reactions and hydroesterification reactions of olefins and the reactions for the syntheses of esters, amides, aldehydes and the like by the carbonylation of organic halogen compounds and suitable catalysts include various kinds of metal catalysts and metal compound catalysts. Particularly preferable catalysts in the reaction of the inventive method are the metals belonging to the VIIIth group in the Periodic Table such as iron, cobalt, nickel, ruthenium, rhodium, platinum, palladium and the like as well as compounds thereof. From the standpoint of the larger reaction velocities, more preferable are those containing palladium or nickel.

Suitable palladium catalysts are exemplified by metallic palladium such as palladium black, metallic palladium supported on a carbon carrier and the like; complexes of zero-valent palladium complex such as tetrakis(triphenylphosphine)palladium, tetrakis(triphynilarsine)palladium, dibenzylideneacetonepalladium, carbonyltris(triphenylphosphine)palladium, maleic anhydridebis(triphenylphosphine)palladium and the like; salts and complexes of divalent palladium such ad dichlorobis(triophenylphosphine)palladium, dichlorobis(benzonitrile)palladium, dibromobis(triphenylarsine)palladium, dichloro-1,1'-bis(diphenylphosphino)ferrocenepalladium, dichloro-1,1'-bis(diphenylarsino)ferrocenepalladium, dichloro-α,ω-bis(diphenylphosphino)alkanepalladium of which the alkane has a straight chain, branched chain or cyclic chain structure with 1 to 10 carbon atoms, dichloro-α,α'-bis(-diphenylphosphino)-o-xylenepalladium, palladium chloride, palladium acetate, bis(acetato)bis(triphenylphosphine)palladium and the like; and complexes of organic palladium or hydrogenated palladium such as iodophenylbis(triphenylphosphine)palladium, iodo-p-tolylbis(triphenylarsine)palladium, chlorobenzoylbis(-triphenylphosphine)palladium, iodomethylbis(tributylphosphine)palladium, dimethylbis(diphenylphosphino)ethanepalladium, dihydridobis(tricyclohexylphosphine)palladium and the like. Any precursor compounds also can be used provided that the compound may produce a organopalladium halide species in the reaction system by the reaction with the organic halogen compound. It is further optional that the above named catalysts are used in the reaction with admixture of a ligand such as phosphines, phosphinites, phosphites, arsines, stibines, tertiary amines, pyridine bases, bipyridyl and the like.

The nickel catalysts used satisfactorily in the reaction, on the other hand, include nickel carbonyl and the complexes thereof obtained by the substitution of a Lewis base such as amines, phosphines and arsines for part or all of the coordinating carbon monoxide therein. Exemplary of such catalysts are tricarbonyltriphenylphosphinenickel, dicarbonylbis(triphenylphospphine)nickel, carbonyltris(triphenylphosphine)nickel, tetrakis(triphenylphosphine)nickel, dicarbonylbis(triphenylarsine)nickel, dicarbonyl-α,ω-bis(diphenylphosphino)alkanenickel of which the alkane has a straight chain or branched chain or cyclic chain structure with 2 to 10 carbon atoms, dicarbonyl-1,1'-bis(diphenylphosphino)ferrocenenickel and the like. It is of course that a precursor compound capable of being readily converted into the above named complex in the reaction mixture is used as exemplified by metallic nickel, nickel chloride, dichlorobis(triphenylphosphine)nickel, dichlorobis(triphenylarsine)nickel, dibromo-1,1'-bis(diphenylphosphino)ferrocenenickel and the like. It is further optional that the above named precursor compound is replaced with a combination of a suitable salt of nickel and a Lewis base capable of readily forming the precursor compound in the reaction mixture. The nickel salts suitable in this case include inorganic salts of divalent nickel such as nickel chloride, nickel bromide and the like, and salts of nickel with organic acids such as nickel acetate and the like while the Lewis bases suitable in this case include various kinds of amines, phosphines, diphosphines, arsines and stibines. In addition, several carbonylation catalysts containing other kind of metals may be used in a similar form to the above. Examples of such catalyst include, for example, dichlorobis(triphenylphosphine)platinum, tricarbonylbis(triphenylphosphine)ruthenium, iron pentacarbonyl, dicobaltoctacarbonyl, cyclopentadienyldicarbonyl cobalt, chlorocarbonylbis(triphenylphosphine)rhodium, chlorodicarbonylrhodium dimer and the like.

The reaction according to the inventive method can proceed regardless of the presence or absence of a solvent in the reaction mixture. When the reaction is performed by diluting the reaction mixture with a solvent, hexane, benzene, ether, tetrahydrofuran, hexamthylphosphotriamide, dimethylformamide, acetonitrile, acetone and the like are used satisfactorily although any other kinds of conventional organic solvents can be used for the purpose provided that the solvent does not serve as a source of active protons such as alcohols, carboxylic acids and the like.

The reaction according to the inventive method can be carried out under about the same reaction conditions as in conventional carbonylation reactions. The partial pressure of carbon monoxide is determined depending on the type of the catalyst used in the reaction and it should be usually in the range from atmospheric or below to 200 atmospheres or, preferably, from atmospheric to 50 atmospheres. Higher partial pressures of carbon monoxide are in general advantageous due to the increase in the yield of the desired product although an excessively high partial pressure of carbon monoxide may result in the decreased reaction velocity in addition to the disadvantages caused by the increased investment for the apparatus. If desired, the carbon monoxide used in the reaction may be diluted with an inert gas such as nitrogen, methane and the like.

The molar ratio of the halogen-containing organic compound and the primary amine may deviate from the stoichiometry considerably since the proceeding of the reaction is not disturbed by the presence of an excess amount of either one of the reactants in the reaction mixture over the other. Usually the molar ratio of the halogen-containing organic compound to the primary amine is selected in the range from 50:1 to 1:500. It is also an advantageous embodiment of the inventive method that the amine is used in large excess over the halogen compound so that the amine serves also as a solvent for the reaction mixture.

The amount of the catalyst to be added to the reaction mixture should be determined in consideration of the reactivity of the halogen-containing organic compound though not particularly limitative. The molar ratio of the catalyst to the halogen compound is usually 1:10 or smaller or, preferably, in the range from 1:30 to 1:3000.

The reaction of the present invention can proceed even at room temperature though dependent on the structure of the halogen-containing organic compound but it is optional that the reaction mixture is heated at a temperature up to 300° C. when acceleration of the reaction is desired. It should be noted, however, that an excessively high temperature of the reaction mixture may cause formation of a carboxylic acid amid as a by-product, the amount thereof being larger at higher reaction temperatures. Furthermore, the α-ketoamide imine as the desired product may be gradually decomposed at an excessively high temperature. Therefore, the reaction temperature should be determined taking the side reaction and the thermal decomposition reaction into consideration, usually, in the range from 30° to 200° C.

The α-ketoamidoimine produced by the reaction of the inventive method is readily separated from the reaction mixture and purified by a procedure in which the reaction mixture is first subjected to the solid-liquid separation such as centrifugal separation or filtration or washing with water to remove the precipitated salt formed as a by-product followed by a conventional purification treatment such as distillation, recrystallization and the like.

In the method of the present invention, a wide variety of the halogen-containing organic compounds and the primary amines can be used in the reaction so that various kinds of the α-ketoamide imines can be readily obtained. In addition, the procedure of the reaction is very easy because no complicated or troublesome steps are involved in the reaction procedure and the reaction can be performed without the use of any highly reactive starting reactants such as organic lithium compounds, Grignard reagents and the like.

The method of the present invention will be more fully understood when the examples given below are referred to.

EXAMPLE 1

Into an autoclave of 27 ml capacity made of stainless steel were introduced $1.88 \times 10^{-2}$ mmoles of palladium chloride, 4 mmoles of iodobenzene and 3 ml of cyclohexyl amine under an atmosphere of nitrogen followed by the introduction of carbon monoxide up to a pressure of 40 atmospheres at room temperature and the reaction was undertaken for 2 hours at 100° C. The gas chromatographic analysis of the reaction mixture after completion of the reaction using a SE-30 column of 40 ml length gave a result that the N'-cyclohexylimine of N-cyclohexylbenzoylformamide had been formed in a yield of 81.4% accompanied by a by-product of N-cyclohexylbenzamide in a yield of 12.9%. The reaction mixture was added to a mixture of water and ether and the ether solution in the upper layer was taken and evaporated to dryness followed by recrystallization of the residue from ether solution to give crystals of N-cyclohexylbenzoylformamide N'-cyclohexylimine having a melting point of 160° to 163° C. The yield of the product after isolation was 78.1%.

EXAMPLES 2–14

Reactions were undertaken with a variety of combinations of the halogen compounds, amines and catalysts in substantially the same manner as in Example 1. The results of the experiments are summarized in the Table below. The values of the yield in the table were calculated from the gas chromatographic data.

| Ex. No. | Halogen cpd. $R^1X$ (4 mmol) | Amine $R^2NH_2$ (3 ml) | Catalyst ($1.88 \times 10^{-2}$ mmol) | Reaction temp. (°C.) | CO pressure (atm) | Reaction time (hrs.) | Yield of $R^1-\underset{\underset{R^2}{\overset{\|}{N}}}{C}-CONHR^2$ (%) |
|---|---|---|---|---|---|---|---|
| 2 | $C_6H_5I$ | $n\text{-}C_6H_{13}NH_2$ | $PdCl_2$ | 100 | 40 | 2 | 39 |
| 3 | $C_6H_5I$ | $n\text{-}C_4H_9NH_2$ | $PdCl_2$ | 100 | 40 | 2 | 34 |

-continued

| Ex. No. | Halogen cpd. $R^1X$ (4 mmol) | Amine $R^2NH_2$ (3 ml) | Catalyst ($1.88 \times 10^{-2}$ mmol) | Reaction temp. (°C) | CO pressure (atm) | Reaction time (hrs.) | Yield of $R^1-\underset{\underset{\underset{R^2}{\diagdown}}{N}}{\overset{\|}{C}}-CONHR^2$ (%) |
|---|---|---|---|---|---|---|---|
| 4 | $C_6H_5I$ | $n\text{-}C_4H_9NH_2$ | $PdCl_2(dppb)^{*1}$ | 60 | 40 | 3 | 17 |
| 5 | $C_6H_5I$ | $iso\text{-}C_3H_7NH_2$ | $PdCl_2$ | 100 | 40 | 3 | 79 |
| 6 | $C_6H_5Br$ | ⟨H⟩—$NH_2$ | $PdCl_2(dppb)^{*1}$ | 100 | 20 | 46 | 75 |
| 7 | $C_6H_5CH_2Cl$ | ⟨H⟩—$NH_2$ | $PdCl_2(dppb)^{*1}$ | 60 | 20 | 16 | 8 |
| 8 | $ClCH_2COOC_2H_5$ | $C_6H_5CH_2NH_2$ | $PdCl_2(dppb)^{*1}$ | 80 | 40 | 15 | 11 |
| 9 | 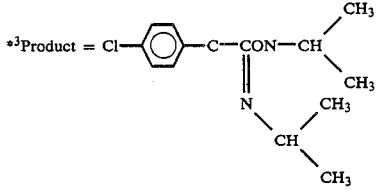 | ⟨H⟩—$NH_2$ | $PdCl_2(dppb)^{*1}$ | 100 | 20 | 5 | 37 |
| 10 | $CH_3O$—⟨○⟩—I | ⟨H⟩—$NH_2$ | $PdCl_2(dppf)^{*2}$ | 100 | 40 | 3 | 16 |
| 11 | $C_6H_5I$ | ⟨H⟩—$NH_2$ | $Pd(OAc)_2$ | 100 | 40 | 3 | 42 |
| 12 | $C_6H_5I$ | ⟨H⟩—$NH_2$ | $PdCl_2(As\phi_3)_2$ | 80 | 40 | 2 | 21 |
| 13 | 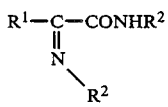 | ⟨H⟩—$NH_2$ | $PdCl_2(dppb)^{*1}$ | 80 | 30 | 10 | 45 |
| 14 | $Cl$—⟨○⟩—$Br$ | $iso\text{-}C_3H_7NH_2$ | $PdCl_2$ | 100 | 20 | 2 | 81*3 |

*1dppb = 1,4-bis(diphenylphosphino)butane
*2dppf = 1,1'-bis(diphenylphosphino)ferrocene

*3Product = $Cl$—⟨○⟩—$\underset{\underset{N}{\|}}{C}$—$CON$—$CH\underset{CH_3}{\overset{CH_3}{\diagup}}$ ...

(product structure with $CH$, $CH_3$, $CH_3$ groups)

What is claimed is:

1. A method for the preparation of an α-ketoamide imine represented by the formula:

$$R^1-\underset{\underset{\underset{R^2}{\diagdown}}{N}}{\overset{\|}{C}}-CONHR^2$$

wherein $R^1$ is a group selected from the group consisting of alkyl, aryl, aralkyl, cycloalkyl, alkenyl and heterocyclic groups optionally substituted with one or more groups selected from the group consisting of alkoxy, alkoxycarbonyl and halogen groups and $R^2$ is a group selected from the group consisting of alkyl, aryl, aralkyl and cycloalkyl groups, which comprises:

reacting a halogen-containing organic compound represented by the formula $R^1X$ selected from the group consisting of bromobenzene, iodobenzene, bromonaphthalene, 4-iodoanisole, 4-acetylbromobenzene, β-bromostyrene, ethyl β-bromoacrylate, 2-bromo-2-butene, 2-methyl-1-bromo-propene, 2-methylthio-1-bromoethylene, benzyl chloride, ethyl chloroacetate, chloromethylimidazole, chloroacetamide, 3-chloromethylindole, and a halogen-containing heterocyclic compound derived from furan, thiophene, pyrrole or pyridine; a primary amine represented by the formula $R^2NH_2$, in which $R^2$ is selected from the group consisting of methyl, ethyl, propyl, butyl, cyclohexyl, benzyl and phenyl 4-tolyl; and carbon monoxide wherein the carbon monoxide reacts with the halogen-containing organic compound and the primary amine under a partial pressure of from 1 atmosphere to 200 atmospheres in the presence of an effective catalytic amount of a carbonylation catalyst to produce a recoverable quantity of said α-ketoamide imine.

2. The method of claim 1, wherein said carbonylation catalyst is nickel or palladium in the metallic state or a compound containing nickel or palladium.

3. The method of claim 1, wherein said halogen-containing organic compound and said primary amine are reacted in a molar ratio in the range of from 50:1 to 1:500.

4. The method of claim 1, wherein the amount of the molar ratio of the carbonylation catalyst to the halogen-containing organic compound is 1:10 or less.

5. The method of claim 1, wherein said halogen-containing organic compound is a halobenzene derivative selected from the group consisting of bromobenzene, iodobenzene, bromonaphthalene, 4-iodoanisole and 4-acetylbromobenzene.

6. The method of claim 1, wherein said halogen-containing organic compound is a halogenated derivative of ethylene selected from the group consisting of β-bromostyrene, ethyl β-bromoacrylate, 2-bromo-2-butene, 2-methyl-1-bromopropene and 2methylthio-1-bromoethylene.

7. The method of claim 1, wherein said halogen-containing organic compound is a halomethane derivative selected from the group consisting of benzyl chloride, ethyl chloroacetate, chloromethylimidazole, chloroacetamide, and 3-chloromethylindole.

8. The method of claim 1, wherein said halogen-containing organic compound is a halogen-containing heterocyclic compound derived from furan, thiophene, pyrrole or pyridine.

9. The method of claim 1, wherein the catalyst is a catalytic metal belonging to Group VIII of the Periodic Table or a compound thereof.

10. The method of claim 1, wherein the partial pressure of carbon monoxide is from atmospheric pressure up to 50 atmospheres.

11. The method of claim 1, wherein said amine is present in an excess over the halogen compound.

12. The method of claim 1, wherein the molar ratio of said catalyst to said halogen compound is in the range of from 1:30 to 1:3000.

13. The method of claim 1, wherein said reaction is carried out at a temperature of from 30° to 200° C.

14. The method of claim 1, wherein the ratio of said catalyst to said halogen compound is in the range of from 1:30 to 1:3000 and the reaction is carried out at a temperature of from room temperature up to 300° C.

* * * * *